(12) United States Patent
Holmes et al.

(10) Patent No.: US 7,476,759 B2
(45) Date of Patent: Jan. 13, 2009

(54) MATRIX METALLOPROTEINASE INHIBITORS

(75) Inventors: Ian Holmes, Stevenage (GB); Stephen Paul Watson, Stevenage (GB)

(73) Assignee: Glaxo Group Limited, Greenford Middlesex (GB)

( * ) Notice: Subject to any disclaimer, the term of this patent is extended or adjusted under 35 U.S.C. 154(b) by 0 days.

(21) Appl. No.: 10/569,812

(22) PCT Filed: Aug. 12, 2004

(86) PCT No.: PCT/EP2004/009087

§ 371 (c)(1),
(2), (4) Date: Feb. 10, 2006

(87) PCT Pub. No.: WO2005/016868

PCT Pub. Date: Feb. 24, 2005

(65) Prior Publication Data

US 2006/0235074 A1   Oct. 19, 2006

(30) Foreign Application Priority Data

Aug. 14, 2003  (GB) ................................. 0319069.1

(51) Int. Cl.
C07C 229/00 (2006.01)
C07C 255/00 (2006.01)
A01N 47/00 (2006.01)
A01N 37/12 (2006.01)
A01N 37/44 (2006.01)

(52) U.S. Cl. ........................ 562/450; 558/410; 514/521; 514/563; 514/562

(58) Field of Classification Search ................. 562/450, 562/430; 514/411; 548/472
See application file for complete search history.

(56) References Cited

U.S. PATENT DOCUMENTS

| 3,644,479 A |   | 2/1972  | Juby et al. |
|---|---|---|---|
| 3,663,627 A |   | 5/1972  | Juby et al. |
| 3,763,229 A |   | 10/1973 | Shunsaku et al. |
| 3,940,434 A |   | 2/1976  | Haas et al. |
| 5,804,581 A | * | 9/1998  | Wolanin ................... 514/237.5 |
| 6,087,392 A | * | 7/2000  | Reiter ........................ 514/459 |

(Continued)

FOREIGN PATENT DOCUMENTS

DE        2023000        8/1971

OTHER PUBLICATIONS

Goodman & Gilman's The Pharmacological Basis of Therapeutics. 10th ed. NY McGraw Hill 2001 p. 3.*
Shapiro (Thrombosis and Homeostasis, 82: 846-849, 1991).*
Newby (Current Opinion in Lipidology, 17:556-61, 2006).*

Allen, G.R., Jr., Littell, R., McEvoy, F.J., Sloboda, A.E., "5-Substituted-1-indancarboxylic Acids as Potential Anti-inflammatory Agents", J. Med. Chem., vol. 15, No. 9, 1972, pp. 934-937, XP001204841.

(Continued)

*Primary Examiner*—Daniel M Sullivan
*Assistant Examiner*—Louisa Lao
(74) *Attorney, Agent, or Firm*—Grace C. Hsu; Mary E. McCarthy; Charles M. Kinzig

(57) ABSTRACT

Compounds of Formula (I):

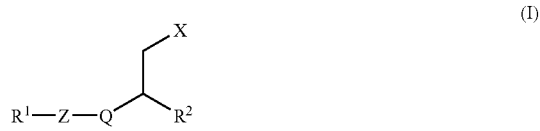

wherein:
$R^1$ is optionally substituted —$C_{4-12}$ alkyl, —$C_{2-10}$alkylcycloalkyl, —$C_{2-6}$alkylheterocycloalkyl, —$C_{2-6}$alkylaryl, optionally substituted 5- or 6-membered aryl or heteroaryl with the proviso that $R^2$ in not pyridinyl;
Z is a bond, $CH_2$, O, S, SO, $SO_2$, $NR^4$, $OCR^4R^5$ or $CR^4R^5O$; or Z, $R^1$ and Q together form an optionally substituted fused tricyclic group;
Q is an optionally substituted 5- or 6-membered aryl or heteroaryl ring;
X is $COR^3$;
$R^2$ is $CONH_2$, $CO_2H$, $CO_2R^7$, $SO_2R^7$ or $SO_2NR^8R^9$, with the proviso that $R^2$ is not $CO_2R^7$, when X is $CONH_2$;
$R^3$ is $OR^6$ or $NR^8R^9$;
$R^4$ and $R^5$ each independently is H, $C_{1-6}$ alkyl or $C_{1-4}$ alkylaryl;
$R^6$ is H or $C_{1-6}$ alkyl;
$R^7$ is $C_{1-6}$ alkyl; and
$R^8$ and $R^9$ each independently is H or $C_{1-6}$ alkyl; or $R^8$ and $R^9$ together with the nitrogen atom to which they are attached form a 5- or 6-membered ring which may optionally include 1 or more further heteroatoms selected from O, S and N;
or
physiologically functional derivatives thereof, with the proviso that formula (I) compounds are not:
[3-(acetylamino)-4-cyclohexylphenyl]-butanedioic acid and 3-(acetylamino)-4-cyclohexylphenyl]-butanedioic acid diethyl ether;
butanedioic acid [3-methoxy-4-(phenylmethoxy)phenyl]; or
butanedioic acid [4-(phenylmethoxy)phenyl]; and
with the proviso that when $R^1$ is $C_{4-12}$alkyl, Z is other than a bond, O or $CH_2$;
and physiologically functional derivatives thereof, processes for their preparation, pharmaceutical formulations containing them and their use as inhibitors of matrix metallproteinase enzymes (MMPs) are described.

5 Claims, No Drawings

U.S. PATENT DOCUMENTS

| | | | | |
|---|---|---|---|---|
| 6,130,220 | A * | 10/2000 | Broka et al. | 514/255.01 |
| 6,143,744 | A * | 11/2000 | Broka et al. | 514/238.2 |
| 6,156,798 | A * | 12/2000 | Reiter | 514/562 |
| 6,197,810 | B1 * | 3/2001 | Reiter | 514/459 |
| 6,342,521 | B1 * | 1/2002 | Reiter | 514/472 |
| 6,372,758 | B1 * | 4/2002 | DeCrescenzo et al. | 514/316 |
| 6,380,239 | B1 * | 4/2002 | Muller et al. | 514/417 |
| 6,387,901 | B1 * | 5/2002 | Chupak | 514/237.5 |
| 6,765,003 | B1 * | 7/2004 | Mantegani et al. | 514/183 |
| 2001/0014688 | A1 * | 8/2001 | Barta et al. | 514/318 |
| 2001/0039287 | A1 * | 11/2001 | Barta et al. | 514/330 |
| 2001/0041710 | A1 * | 11/2001 | Robinson et al. | 514/278 |
| 2001/0049449 | A1 * | 12/2001 | Becker et al. | 548/537 |
| 2005/0256116 | A1 * | 11/2005 | Clary et al. | 514/232.5 |

OTHER PUBLICATIONS

G. Arsenault, A.D. Broadbent, P. Hutten-Czapski, "Enolate Ion Reaktions of Leucoquinizarin. Michael Additions", J. Chem. Soc., Chem. Commun., 1983, pp. 437-438, XP009043011.

Avetisyan, et al., "Relationship Between Chemical Structure and Anticonvulsant Activity in Succinimides", Pharm. Chem. J., vol. 22, No. 4, 1988, pp. 309-313, XP009042966.

Barnett, et al., "The Action of Maleic Anhydride Upon Some Anthracene Derivatives", J. Chem. Soc., 1934, pp. 1224-1226, XP009042990.

H.J. Bestmann, H.J. Lang, "Zur Reaktian von Alkiliden. triphenylphosphoranen Mit Chinonen", Tetrahedron Letters, vol. 25, 1969, pp. 2101-2106, XP001205101.

P. Cagniant, N. Bellinger, D. Cagniant, "Contribution al'etude de Quelques Derives Substitutes en 1 du Dibenzoselenophene, Nouvelle Synthese du Beno-ub! Naphto-'1,2d! Selenophene", C.R. Acad. SC. Paris, T.277, Serie C., Oct. 29, 1973, pp. 779-781, XP009042974.

H. Gotthardt, S. Niebrla, "Thermische Reaktionen von Thioketonen Mit Acetylendicarbonsaure-dimethylester", Liebigs Ann. Chem., 1980, pp. 867-872, XP009042968.

P.F. Juby, W.R. Goodwin, T. W. Hudyma, R.A., Partyka, "Anti-inflammatory Activity of Some Indian-1-carboxylic Acids and Related Compounds", J. Med. Chem., vol. 15, No. 12, 1972, pp. 1297-1306, XP001204917.

Y. Tamura, Y. Shirouchi, J. Minamikawa, J. Haruta, "Synthesis of 2-Arylsuccinates by Oxidative 1, 2-Aryl Migration of 3-Aroylprpionic Acids or 5-Arylfuran-2 (3h)-ones with Thallium (III) Nitrate", Chem. Pharm. Bull., vol. 33, No. 2, 1985, pp. 551-556, XP001204918.

E.C., Taylor, R.A., Conely, A.H., Katz, "Thallium in Organic Synthesis 62. A convenient Synthesis of Alpha-arylsuccinic Acids", J. Org. Chem., vol. 49, 1984, pp. 3840-3841, XP001204842.

T. Ueda, I. Ito, Y. Iitaka, "Syntheses of Pyrazole derivatives. Reaction of 1-Methyl-2-phenyl-1,2,3,10-tetrahydro-4H-b Enzo '6, 7!thiepino'3,4-c!pyrazole-3,4-dione with Dimethyl Acetylenedicarboxylate", Chem. Pharm. Bull, vol. 24, No. 4, 1976, pp. 596-606, XP009042969.

Allen et al., "5-Substituted-1-Indanecarboxylic Acids as Potential Antiinflammatory Agents", J. Med. Chem., 1972, vol. 15, No. 9, pp. 934-937.

Bestmann et al., "Reaction of Alkylidene Triphenylphosphoranes With Quinones", Tetrahedron Letters, 1969, (25), pp. 2101-2106 (STN: HCAPLUS Abstract 1969:461133; Original Document and Full English Translation).

Brummer et al., "Antibody-Catalyzed Hydrolysis of Oligomeric Esters: A Model for the Degradation of Polymeric Materials", Chem. Commun., 2001, pp. 19-20.

Cagniant et al., "1-Substituted Derivatives of Dibenzoselenophene. New Synthesis of Benzo[b]naphtha[1,2-d]selenophene", Sciences Chimiques, 1973, 277(17), pp. 779-781 (STN: HCAPLUS Abstract 1974:70642; Original Document and Full English Translation).

Cain et al., "Extended Scope of in situ Iodotrimethylsilane Mediated Selective Reduction of Benzylic Alcohols", Chem. Commun., 2001, 00, pp. 1168-1169.

Gotthardt et al., "Thernal Reactions of Thioketones with Dimethyl Acetylenecarboxylate", Liebigs Annalen der Chemie, 1980, (6), pp. 867-872 (STN: HCAPLUS Abstract 1980:639156; Original Document and Full English Translation).

* cited by examiner

MATRIX METALLOPROTEINASE INHIBITORS

This application claims is a 371 of International Application No. PCT/EP2004/009087, filed 12 Aug. 2004.

This invention relates to novel chemical compounds, processes for their preparation, pharmaceutical formulations containing them and their use in therapy. The compounds of the invention are inhibitors of matrix metalloproteinase enzymes (MMPs).

Matrix metalloproteinase enzymes play a major role in extracellular matrix component degradation and remodelling. Examples of MMPs include collagenase 1, 2 and 3, gelatinase A and B, stromelysin 1, 2 and 3, matrilysin, macrophage metalloelastase, enamelysin and membrane type 1,2,3 and 4 MMP. The enzymes are secreted by connective tissue cells and inflammatory cells. Enzyme activation can not only initiate tissue damage but induce increased inflammatory cell infiltration into the tissue, leading to more enzyme production and subsequent tissue damage. For example, elastin fragments produced by MMP degradation are believed to stimulate inflammation by attracting macrophages to the site of MMP activity. Inhibition of MMPs provides a means for treating disease states wherein inappropriate metalloprotease activity results in degradation of connective tissue and inflammation.

International patent application publication number WO97/18188 discloses biphenyl hydroxamate compounds which are said to inhibit MMPs including stromelysin, and tumor necrosis factor α (TNFα). The compounds are reported to have a broad spectrum of activity and inhibit all MMPs.

Certain compounds which are structurally similar to compounds of the present invention are disclosed as intermediates in J Med Chem 1972, 15(9), 934-7.

In one aspect, the present invention provides compounds of formula (I):

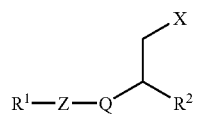

(I)

wherein $R^1$ represents optionally substituted —$C_{4-12}$ alkyl, —$C_{2-10}$alkylcycloalkyl, —$C_{2-6}$ alkyl heterocycloalkyl, —$C_{2-6}$alkylaryl, optionally substituted 5- or 6-membered aryl or heteroaryl, except pyridinyl.

Z represents a bond, $CH_2$, O, S, SO, $SO_2$, $NR^4$, $OCR^4R^5$, $CR^4R^5O$, or Z, $R^1$ and Q together form an optionally substituted fused tricyclic group;

Q represents an optionally substituted 5- or 6-membered aryl or heteroaryl ring;

X represents $COR^3$;

$R^2$ represents $CONH_2$, $CO_2H$, $CO_2R^7$, $SO_2R^7$ or $SO_2NR^8R^9$, except that $R^2$ may not represent $CO_2R^7$ when X is $CONH_2$;

$R^3$ represents $OR^6$, or $NR^8R^9$;

$R^4$ and $R^5$ each independently represents H, $C_{1-6}$ alkyl or $C_{1-4}$ alkylaryl;

$R^6$ represents H or $C_{1-6}$ alkyl;

$R^7$ represents $C_{1-6}$ alkyl;

$R^8$ and $R^9$ each independently represents H or $C_{1-6}$ alkyl or $R^8$ and $R^9$ together with the nitrogen atom to which they are attached form a 5- or 6-membered ring which may optionally include 1 or more further heteroatoms selected from O, S and N; and physiologically functional derivatives thereof with the exception of [3-(acetylamino)-4-cyclohexylphenyl]-butanedioic acid and 3-(acetylamino)-4-cyclohexylphenyl]-butanedioic acid diethyl ether;

butanedioic acid [3-methoxy-4-(phenylmethoxy)phenyl];
butanedioic acid [4-(phenylmethoxy)phenyl];
with the proviso that when $R^1$ represents $C_{4-12}$ alkyl, Z is other than a bond, O or $CH_2$;

and physiologically functional derivatives thereof.

We have found that compounds of formula (I) are potent inhibitors of MMPs.

Advantageously the present compounds are also selective, in particular, they are selective inhibitors of MMP-12.

References to 'aryl' include references to monocyclic carbocyclic aromatic rings (e.g. phenyl) and bicyclic carbocyclic aromatic rings (e.g. naphthyl) and references to 'heteroaryl' include references to mono- and bicyclic heterocyclic aromatic rings containing 1-3 hetero atoms selected from nitrogen, oxygen and sulphur. Examples of monocyclic heterocyclic aromatic rings include e.g. pyrimidinyl, thienyl, furanyl, pyrrolyl, oxazolyl, isoxazolyl, oxadiazolyl, thiazolyl, thiadiazolyl or imidazolyl, and examples of bicyclic heterocyclic aromatic rings include e.g. benzimidazolyl, quinolinyl or indolyl. Carbocyclic and heterocyclic aromatic rings may be optionally substituted, e.g. by one or more $C_{1-6}$ alkyl, $C_{2-6}$ alkenyl, halogen, $(CH_2)_{0-4}OR^{10}$, $(CH_2)_{0-4}SR^{10}$, $SO_2R^{11}$, $COR^{11}$, aryloxy, thioaryl, cyano, hydroxy, nitro, $NR^{10}R^{12}$, —$NR^{10}COR^{12}$, —$OCF_3$, —$CF_3$, $COOR^{10}$, —$OCHCF_2$, —$SCF_3$, —$CONR^{10}R^{12}$ —$SO_2NR^{10}R^{12}$, or like groups, wherein $R^{10}$ and $R^{12}$ independently represents H or $C_{1-6}$ alkyl, and $R^{11}$ represents $C_{1-6}$ alkyl.

References to alkyl include references to both straight chain and branched chain aliphatic isomers of the corresponding alkyl. It will be appreciated that references to alkylene and alkoxy shall be interpreted similarly.

References to cycloalkyl include $C_{3-8}$ cycloalkyl such as cyclopropyl, cyclopentyl and cyclohexyl.

References to heterocycloalkyl include $C_{3-8}$ heterocycloalkyl such as pyrrolidinyl, piperidinyl and piperazinyl.

Suitably, $R^1$ represents substituted or unsubstituted aryl, indolyl or thienyl, such as substituted or unsubstituted phenyl.

Suitably $R^2$ represents $CONH_2$ or $COOH$ or $CO_2CH_3$.

Suitably $R^3$ represents OH or $NH_2$, more preferably OH.

In one preferred subgroup of compounds according to the invention, X represents $CO_2H$ and $R^2$ represents $CONH_2$.

Suitably Q represents unsubstituted aryl, such as unsubstituted phenyl.

Suitably Z represents a bond or O.

A further preferred subgroup of compounds of formula (I) is represented by formula (Ia):

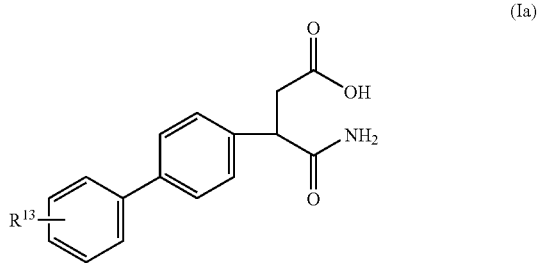

(Ia)

wherein $R^{13}$ represents H, halo, $CF_3$, —$OCF_3$, cyano, nitro, $OR^{14}$, $SR^{15}$ or $COR^{16}$;

$R^{14}$, $R^{15}$, $R^{16}$ independently represent H, $C_{1-6}$ alkyl or $C_{1-4}$ alkylaryl;

and physiologically functional derivatives thereof.

Preferably $R^{13}$ is in the meta or para position.

Preferably $R^{14}$ represents methyl or $CF_3$.

Preferably $R^{15}$ represents methyl.

Preferably $R^{16}$ represents methyl.

By the term "physiologically functional derivative" is meant a chemical derivative of a compound of formula (I) having the same physiological function as the free compound of formula (I), for example, by being convertible in the body thereto and includes any pharmaceutically acceptable esters, amides and carbamates, salts and solvates of compounds of formula (I) which, upon administration to the recipient, are capable of providing (directly or indirectly) compounds of formula (I) or active metabolite or residue thereof.

Suitable salts of the compounds of formula (I) include physiologically acceptable salts and salts which may not be physiologically acceptable but may be useful in the preparation of compounds of formula (I) and physiologically acceptable salts thereof. If appropriate, acid addition salts may be derived from inorganic or organic acids, for example hydrochlorides, hydrobromides, sulphates, phosphates, acetates, benzoates, citrates, succinates, lactates, tartrates, fumarates, maleates, 1-hydroxy-2-naphthoates, palmoates, methanesulphonates, formates or trifluoroacetates.

Examples of solvates include hydrates.

When compounds of formula (I) contain chiral centres, the invention extends to mixtures of enantiomers (including racemic mixtures) and diastereoisomers as well as to individual enantiomers. Generally it is preferred to use a compound of formula (I) in the form of a purified single enantiomer.

The compounds of formula (I) and salts and solvates thereof may be prepared by the methodology described hereinafter, constituting a further aspect of this invention.

The invention also includes processes for the preparation of compound of formula (I), which comprises a process:

(A) preparing a compound of formula (I), wherein Z represents a bond and $R^1$ represents optionally substituted 5- or 6-membered aryl or heteroaryl, by reacting a compound of formula (II):

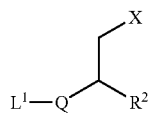

(II)

wherein $R^2$, Q and X are as previously defined for formula (I) and $L^1$ represents a leaving group, with a reagent suitable to introduce the group $R^1$, such as a compound $R^1B(OH)_2$; or (B)(i) for preparing compounds of formula (I), wherein Z represents, O, S, SO, $SO_2$, $NR^4$, $OCR^4R^5$, by reacting a compound of formula (III):

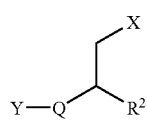

(III)

wherein $R^2$, Q and X are as previously defined for formula (I) and Y represents OH, SH, $NHR^4$, $HOCR^4R^5$, with a compound of formula (IV)

(IV)

wherein $R^1$ is defined above for compounds of formula (I) and $L^2$ represents a leaving group; and (ii) wherein Y is —SH optionally followed by oxidizing the Y group to the corresponding SO or $SO_2$ group as required; or (C) for preparing compounds of formula (I), wherein Z is —$CR^4R^5O$— by reacting a compound of formula (III), wherein Y is —OH, with a compound of formula (V)

(V)

wherein $R^1$ $R^4$, $R^5$ are defined above for compounds of formula (I) and $L^3$ represents a leaving group;

(D) for preparing compounds of formula (I), wherein Z is $CH_2$ and $R^1$ represents optionally substituted 5- or 6-membered aryl or heteroaryl, by reacting (i) a compound of formula (VII)

(VI)

wherein Q, X and $R^2$ are as defined above, with an optionally substituted 5- or 6-membered aryl or heteroaryl nucleophile, for example, a compound of formula (VII);

(VII)

wherein A is a 5- or 6-membered aryl or heteroaryl, $R^{17}$ is H or one or more substituents, which have been described earlier in the specification, and M is a metal, for example, Mg, Li or MgLi; and (ii) by reducing and eliminating of the resultant alcohol or;

(E) by deprotecting of a protected form of the compounds of formula (I).

Process (A) may be performed in the presence of a catalyst, such as a noble metal catalyst e.g. palladium, and a suitable base, such as an alkali metal carbonate, e.g. caesuim carbonate or preferably potassium carbonate. The reaction is conveniently carried out in a suitable solvent, such as a polar organic solvent, e.g. dimethyl formamide (DMF) or DME (dimethoxy ethane). Suitable leaving groups represented by $L^1$ include halides, especially bromide or iodide.

Process (B)(i) may be performed in under basic conditions, for example, in the presence of an aqueous hydroxide such as sodium hydroxide, in a suitable solvent, such as an alcohol solvent e.g. ethanol at a non-extreme temperature such as 0 to 100° C. preferably 70° C.

The optional oxidation of the thiol product of step (B)(ii) to the corresponding sulfone may be effected by methods known the person skilled in the art such as oxidation with hydrogen peroxide under standard conditions, whereas the corresponding sulfoxide may be prepared using, for example, Oxone® (potassium peroxymonosulfate) as the oxidising agent under standard conditions or meta-chloro perbenzoic acid in a suitable solvent such as $CH_2Cl_2$.

Process (C) may be performed under condition analogous to those described above for process (B)(i).

Process (D) may be performed under anhydrous conditions preferably in an inert atmosphere such as nitrogen, in a suitable solvent, for example THF or diethyl ether at a reduced temperature such as −78° C. followed by warming to room temperature.

The reduction and elimination of the resultant alcohol group may be effected using trimethylsilyl chloride and sodium iodide in a solvent such as acetonitrile at a non-extreme temperature such as room temperature, for example, as explained in *Chem. Com.* 2001, 13, 1168-69.

It will be appreciated by those skilled in the art that compounds of formula (I) may also be prepared from other compounds of formula (I) by interconversion using processes such as oxidation, reduction, substitution, deprotection etc, standard in the art of synthetic chemistry.

Protecting groups may be any conventional protecting groups, for example as described in "Protective Groups in Organic Synthesis" by Theodora Greene and Peter G. M. Wuts (John Wiley and Sons Inc. 1999). Suitable carboxylic acid protecting groups include, but are not limited to, carboxylic acid esters, for example, methyl ester, ethyl ester, t-butyl ester, aryl esters e.g. benzyl ester.

Benzyl esters may, for example, be removed by hydrogenolysis in the presence of a catalyst such as $PtO_2$ in a suitable solvent, for example, an alcohol such as ethanol at a non-extreme temperature. t-Butyl esters may be removed, for example, by $SiO_2$ in a suitable solvent such as toluene at a non-extreme temperature.

Compound of formula (II) may be prepared by a process comprising (F) preparing a compound of formula (II) wherein X is COOH and $R^2$ is COOH by deprotection of a compound of formula (VIII)

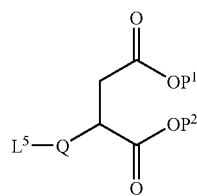

(VIII)

wherein

Q is as defined above for compounds of formula (I), $L^5$ represents a leaving group for example halogen such as chloro or bromo or a masked derivative thereof such as a protected alcohol and $P^1$ and $P^2$ independently represent a protecting group by removal of the protecting groups $P^1$ and $P^2$; and if necessary deprotection and/or conversion of $L^5$ into a good leaving group; or (G) preparing a compound of formula (II) wherein X is $COR^3$ by deprotection of a compound of formula (VIII) by selective removal of $P^1$;

amination or esterifiction of the resultant carboxylic acid, under standard conditions;

followed by removal of the protecting group $P^2$ by appropriate means;

subsequent treatment with an esterifying agent or aminating agent as desired, for example, an alkoxy nucleophile or ammonia; and if necessary deprotection and/or conversion of $L^5$ into a good leaving group;

(H) preparing a compound of formula (II) wherein $R^2$ is an ester $CONH_2$ and X is a carboxyclic acid may be prepared by selective deprotection of compounds of formula (VIII) to remove $P^2$;

subsequent treatment with an esterifying agent or aminating agent as desired, for example, an alkoxy nucleophile or ammonia;

if necessary conversion of $L^5$ into a good leaving group;
removal of $P^1$ to yield the free carboxylic acid; and
subsequent treatment with an esterifying agent or aminating agent as desired, for example, an alkoxy nucleophile or ammonia, under standard conditions above; or (I) preparing compounds of formula (II) wherein X and $R^2$ are the same may be effected by deprotection of a compound of formula (VIII) and subsequent amination or esterification with at least two molar equivalents of an appropriate reagent;

(J) preparing a compound of formula (II) wherein $R^2$ represents $SO_2R^7$ or $SO_2NR^8R^9$ by (i) oxidising a compound of formula (IX)

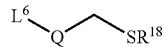

(IX)

wherein Q is as defined above, $L^6$ represents a leaving group, for example, halogen such as chloro or bromo or a masked derivative thereof such as a protected alcohol and $R^{18}$ represents H or $C_{1-6}$ alkyl, to the corresponding sulfoxide, sulfone or sulfonic acid.

(ii) where the product of step (i) is the sulfonic acid subsequent treatment with a halogenating agent, for example, $POCl_3$ followed by treatment with a compound of formula (X)

$NHR^8R^9$ (X)

wherein $R^6$ and $R^7$ are defined above for compounds of formula (I);

(iii) treatment of the product of step (i) or step (ii) with a compound of formula (XI):

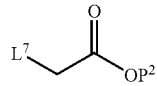

(XI)

wherein $L^7$ represents a leaving group, for example, halogen such as chloro or bromo and $P^2$ represents a protecting group in the presence of a suitable base, for example LiHMDS (Lithium Bis (trimethylsilyl) amide);

(iv) followed by deprotection to give a compound of formula (II).

Process (F) may be effected under standard conditions, as discussed above, for example, in relation to benzyl ethers and t-butyl ethers. Suitable groups for $L^5$ include halogens, such as chloro, bromo and iodo.

Methods of protection and deprotection are described in "Protective Groups in Organic Synthesis" by Theodora Greene and Peter G. M. Wuts (John Wiley and Sons Inc. 1999). Where selective deprotection is required the protecting groups for the different functional groups in the molecule must be chosen so that they can be removed under different conditions, for example, t-butyl esters may be removed in the presence of benzyl ester using $SiO_2$ in a solvent such as toluene.

In process (G) amination may be effected using any suitable reagent under standard conditions, for example, ammonium chloride in a suitable solvent such as dimethyl formamide (DMF) in the presence of an activating agent such as O-(7-azabenzotriazol-1-yl)-N,N,N'N'-tetramethyluronium hexafluorophosphate (HATU) and Diisopropyl ethylamine (DIPEA). Esterification may be effected using any suitable reagent under standard conditions, for example, an alkoxide in a suitable solvent such as an alcohol solvent.

Processes (H) and (I) may be performed under analogous conditions to those described above for process (G).

Process (J)(i) may be performed using, for example, potassium peroxymonosulfate (Oxone®) in a suitable solvent such as water or using meta chloro perbenzoic acid in a solvent such as dichloromethane. The reaction will normally be performed at a non-extreme temperature, for example, 0° C. to 40° C. such as room temperature.

The halogenation step of process (J)(ii) will usually be performed without the addition of solvent at an elevated temperature, for example, 30 to 150° C. such as 105° C. using a reagent such as POCl$_3$. The subsequent amination step will generally be performed in a suitable solvent, for example, THF, DMF or dichloromethane (DCM) in the presence of a weakly or non-nucleophilic base, for example, triethylamine at a non-extreme temperature, for example 0° C. to 100° C. such as room temperature.

Process (J)(iii) will usually be performed at a reduced temperature, for example, −78 to 20° C. such as −78° C. and subsequent warming to 0° C.

The deprotection of step (IV) may be effected by methods well known to persons skilled in the art.

Compounds of formula (III) may be prepared from compounds of formula (XII)

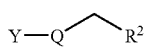

(XII)

or a protected derivative thereof wherein the functionality in group Y and/or group R$^2$ is protected wherein Q, Y and R$^2$ are as defined above for compounds of formula (III) by analogous methodology to that described above for the preparation of compounds of formula (II).

Furthermore, in some instances it may be possible to convert compounds of formula (II) into compounds of formula (III) using for example a hydroxide, thiol, amino, or alkoxy nucleophile and an appropriate protection and deprotection strategy.

Compounds of formula (VII) may be prepared by a transmetalation process well known to persons skilled in the art or compounds such as Grignards reagents can be prepared by addition of magnesium metal to the required aryl/alkyl halide as appropriate under suitable conditions.

The reaction may be performed in a -suitable solvent for example, anhydrous THF, under an inert atmosphere at a non-extreme temperature, for example 10° C. to room temperature.

Compounds of formula (VIII) may be prepared from compounds of formula (XIV)

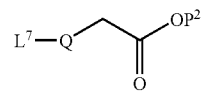

(XIV)

wherein Q and P$^2$ are as defined above and L$^7$ represents a leaving group or a masked leaving group such as a protected alcohol
with a compound of formula (XV)

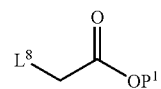

(XV)

wherein P$^1$ is a protecting group as defined above and L$^8$ is a leaving group for example, halogen such as chloro, bromo or iodo.

Compounds of formula (IV), (V), (VI), (X), (XI), (XII), (XIII) and (XV) are known or can be prepared by known methods.

Certain compounds of formula (II), (III), (VII), (VIII), (IX) and (XIV) are new and form an aspect of the invention.

It will be clear to persons skilled in the art that compounds of formula (I) may be prepared by variations of the processes described above wherein the steps are effected in a different order and that protection and deprotection strategies will be adopted as required to yield the desired products and that the order of the steps may be varied as required.

In some instances the leaving groups may be protected as functional derivatives (also referred to as masked derivatives in the specification), for example, as a protected alcohol which can then be converted into a leaving group such as a halogen by a halogenating agent such as POCl$_3$ or SOCl$_2$ or a triflate or mesylate or tosylate by known methods at a latter stage in the synthesis.

The enantiomeric compounds of the invention may be obtained (a) by the separation of the components of the corresponding racemic mixture, for example, by chiral chromatography, enzymatic resolution methods or preparing and separating suitable diastereoisomers, (b) by direct synthesis from the appropriate chiral starting materials by the methods described above, or (c) by methods analogous to those described above using chiral reagents.

Optional conversion of a compound of formula (I) to a corresponding salt may conveniently be effected by reaction with the appropriate acid or base. Optional conversion of a compound of formula (I) to a corresponding solvate or other physiologically functional derivative may be effected by methods known to those skilled in the art.

Compounds of formula (I) may be useful for the treatment of any conditions in which inhibition of matrix metalloproteinase would be beneficial, especially in the treatment of inflammatory diseases and autoimmune disorders.

Examples of inflammatory conditions and autoimmune disorders in which the compounds of the invention have potentially beneficial effects include diseases of the respiratory tract such as asthma (including allergen-induced asthmatic reactions), cystic fibrosis, bronchitis (including chronic bronchitis), chronic obstructive pulmonary disease (COPD), adult respiratory distress syndrome (ARDS), chronic pulmonary inflammation, rhinitis and upper respiratory tract inflammatory disorders (URID), ventilator induced lung injury, silicosis, pulmonary sarcoidosis, idiopathic pulmonary fibrosis, bronchopulmonary dysplasia, arthritis, e.g. rheumatoid arthritis, osteoarthritis, infectious arthritis, psoriatic arthritis, traumatic arthritis, rubella arthritis, Reiter's syndrome, gouty arthritis and prosthetic joint failure, gout, acute synovitis, spondylitis and non-articular inflammatory conditions, e.g. herniated/ruptured/prolapsed intervertebral disk syndrome, bursitis, tendonitis, tenosynovitic, fibromyalgic syndrome and other inflammatory conditions associated with ligamentous sprain and regional musculoskeletal strain, inflammatory disorders of the gastrointestinal tract, e.g. ulcerative colitis, diverticulitis, Crohn's disease, inflammatory bowel diseases, irritable bowel syndrome and gastritis, multiple sclerosis, systemic lupus erythematosus, scleroderma, autoimmune exocrinopathy, autoimmune encephalomyelitis, diabetes, tumor angiogenesis and metastasis, cancer including carcinoma of the breast, colon, rectum, lung, kidney, ovary, stomach, uterus, pancreas, liver, oral, laryngeal and prostate, melanoma, acute and chronic leukemia, periodontal disease, neurodegenerative disease, Alzheimer's disease, Parkinson's disease, epilepsy, muscle degeneration, inguinal hernia, retinal degeneration, diabetic retinopathy, macular degeneration, ocular inflammation, bone resorption diseases, osteoporosis, osteopetrosis, graft vs. host reaction, allograft rejections, sepsis, endotoxemia, toxic shock syndrome, tuberculosis, usual interstitial and cryptogenic organizing pneumonia, bacterial meningitis, systemic cachexia, cachexia secondary to infection or malignancy, cachexia secondary to acquired immune deficiency syndrome (AIDS), malaria, leprosy, leishmaniasis, Lyme disease, glomerulonephritis, glomerulosclerosis, renal fibrosis, liver fibrosis, pancreatitis, hepatitis, endometriosis, pain, e.g. that associated with inflammation and/or trauma, inflammatory diseases of the skin, e.g. dermatitis, dermatosis, skin ulcers, psoriasis, eczema, systemic vasculitis, vascular dementia, thrombosis, atherosclerosis, restenosis, reperfusion injury, plaque calcification, myocarditis, aneurysm, stroke, pulmonary hypertension, left ventricular remodeling and heart failure.

Diseases of principal interest include COPD and inflammatory diseases of the respiratory tract and joints and vascular diseases.

It will be appreciated by those skilled in the art that reference herein to treatment extends to prophylaxis as well as the treatment of established conditions.

There is thus provided as a further aspect of the invention a compound of formula (I) or a physiologically acceptable derivative thereof for use in medicine.

According to another aspect of the invention, there is provided the use of a compound of formula (I) or a physiologically acceptable derivative thereof for the manufacture of a medicament for the treatment of inflammatory conditions or autoimmune disorders.

In a further or alternative aspect there is provided a method for the treatment of a human or animal subject suffering from or susceptible to an autoimmune disorder or an inflammatory condition which method comprises administering to said human or animal subject an effective amount of a compound of formula (I) or a physiologically functional derivative thereof.

The compounds according to the invention may be formulated for administration in any convenient way, and the invention therefore also includes within its scope pharmaceutical compositions comprising a compound of formula (I) or a physiologically acceptable derivative thereof together, if desirable, with one or more physiologically acceptable diluents or carriers.

There is also provided a process for preparing such a pharmaceutical formulation which comprises mixing the ingredients.

The compounds according to the invention may, for example, be formulated for oral, inhaled, intranasal, topical, buccal, parenteral or rectal administration, preferably for oral administration.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maizestarch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminum stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

Compounds according to the invention for topical administration may be formulated as creams, gels, ointments or lotions or as a transdermal patch. Such compositions may for example be formulated with an aqueous or oily base with the addition of suitable thickening, gelling, emulsifying, stabilising, dispersing, suspending, and/or colouring agents.

Lotions may be formulated with an aqueous or oily base and will in general also contain one or more emulsifying agents, stabilising agents, dispersing agents, suspending agents, thickening agents, or colouring agents. They may also contain a preservative.

For buccal administration the compositions may take the form of tablets or lozenges formulated in conventional manner.

The compounds may also be formulated as suppositories, e.g. containing conventional suppository bases such as cocoa butter or other glycerides.

The compounds according to the invention may also be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as antioxidants, buffers, antimicrobial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

The pharmaceutical compositions according to the invention may also be used in combination with other therapeutic agents, for example anti-inflammatory agents (such as corticosteroids (e.g. fluticasone propionate, beclomethasone dipropionate, mometasone furoate, triamcinolone acetonide or budesonide) or NSAIDs (e.g. sodium cromoglycate, nedocromil sodium, PDE-4 inhibitors, leukotriene antagonists, CCR-3 antagonists, iNOS inhibitors, tryptase and elastase inhibitors, beta-2 integrin antagonists and adenosine 2a agonists)) or beta adrenergic agents (such as salmeterol, salbutamol, formoterol, fenoterol or terbutaline and salts thereof) or antiinfective agents (e.g. antibiotics, antivirals).

It will be appreciated that when the compounds of the present invention are administered in combination with other therapeutic agents normally administered by the inhaled or intranasal route, that the resultant pharmaceutical composition may be administered by the inhaled or intranasal route.

Compounds of the invention may conveniently be administered in amounts of, for example, 0.01 to 100 mg/kg body weight, preferably 0.1 to 25 mg/kg body weight, more preferably 0.3 to 5 mg/kg body weight. The compounds may be given more than once daily to be equivalent to the total daily dose. The precise dose will of course depend on the age and condition of the patient and the particular route of administration chosen and will ultimately be at the discretion of the attendant physician.

No toxicological effects are expected when a compound according to the present invention is administered in the above mentioned dose range.

Compounds of the invention may be tested for in vitro activity in accordance with the following assay:

The fluorescent peptide substrate used in the MMP-12 assay is FAM-Gly-Pro-Leu-Gly-Leu-Phe-Ala-Arg-Lys (TAMRA) (SEQ ID. No. 1), where FAM represents carboxyfluorescein, and TAMRA represents tetramethylrhodamine. MMP12 catalytic domain (residues 106-268) protein was expressed in E. coli in the form of insoluble inclusion bodies & stored in concentrated solution under denaturing conditions (8M guanidine hydrochloride). Enzyme was refolded into active form in situ by direct dilution into assay reactions. The 51 uL reactions are run in NUNC-brand black, square 384-well plates, each well containing 2 uM substrate, 20 nM enzyme, and 0.001-100 uM inhibitor, in 50 mM HEPES, pH 7.5, 150 mM NaCl, 10 mM CaCl2, 1 uM ZnAc, 0.6 mM CHAPS, and 2% DMSO. Positive control wells contain no inhibitor. Negative control wells are effected by either pre-dispensing the EDTA quench (see below) or by omitting enzyme. Reactions are incubated at ambient temperature for 120 min, then quenched by the addition of 15 uL of 100 mM EDTA. Product formation in each well is quantified by measuring flourescense with a Molecular Devices Acquest. The excitation wavelength is set at 485 nM, and the emission wavelength is 530 nM. $IC_{50}$ values were obtained by first calculating the percent inhibition (% I) at each inhibitor concentration (% I=100*(1−(I−C2)/(C1−C2)), where C1 is the mean of the positive controls, and C2 is the mean of the negative controls), then fitting the % I vs. inhibitor concentration [I] data to: % I=A+((B−A)/(1+(C/[I]^D))), where A is the lower asymptote, B is the upper asymptote, C is the IC50 value, and D is the slope factor. When tested in this assay, compounds of the Examples had IC50s below 100 micromolar.

The invention may be illustrated by reference to the following examples, which should not be construed as a limitation thereto:

Intermediate 1 tert-Butyl (4-bromophenyl)acetate

Boron trifluoride etherate (0.46 mL) was added in one portion to a stirred solution of bromophenylacetic acid (5.00 g, 23.2 mmol) and t-butyltrichloroacetimidate (10 g, 8.3 mL, 46 mmol) in THF (50 mL) at room temperature under nitrogen. The resulting solution was stirred for 16 h then quenched with saturated sodium hydrogen carbonate solution (50 mL). The resulting suspension was extracted with ethyl acetate (3×50 mL) then the organic extracts combined, dried (magnesium sulfate) and evaporated to dryness. The residue was chromatographed on silica gel (20% diethyl ether:cyclohexane) to give the title compound as a colourless oil (4.93 g, 78%). LC/MS: 3.63 min; z/e 288 and 290, calcd (M+18) 288 and 290. $^1$H NMR (400 MHz: CDCl$_3$): 7.40 (2H), 7.15 (2H), 3.45 (2H), 1.40 (9H).

Intermediate 2

4-Benzyl 1-tert-butyl 2-(4-bromophenyl)succinate

Lithium bis(trimethylsilyl)amide (1.06 M in THF; 18.1 mL, 19.2 mmol) was added dropwise over 10 min to a stirred solution of tert-butyl (4-bromophenyl)acetate (4.92 g, 18.1 mmol) in THF (50 mL) at −78 ° C. under nitrogen. On completion of addition stirring was continued at −78 ° C. for 30 min then benzyl-2-bromoacteate (4.97 g, 3.44 mL, 21.7 mmol) was added dropwise over 5 min. The reaction was allowed to warm slowly to room temperature over 4 h then saturated ammonium chloride solution (50 mL) was added and the resulting suspension extracted with ethyl acetate (3×100 mL). The organic phases were combined, dried (magnesium sulfate) and evaporated to dryness. The residue was chromatographed on silica gel (10% diethyl ether: cyclohexane) to give the title compound as a colourless oil (6.26 g, 82%). LC/MS: 4.02 min; z/e 419 and 421, calcd (M+1) 419 and 421. $^1$H NMR (400 MHz: CDCl$_3$): 7.40 (2H), 7.30 (5H), 7.10 (2H), 5.10 (2H), 3.90 (1H), 3.15 (1H), 2.65 (1H), 1.35 (9H).

Intermediate 3

4-(Benzyloxy)-2-(4-bromophenyl)-4-oxobutanoic acid

A suspension of 4-benzyl 1-tert-butyl 2-(4-bromophenyl) succinate (3.00 g, 7.15 mmol) and silica gel (35.7 g) in toluene (230 mL) was heated at reflux for 3 h. The crude mixture was cooled to room temperature and filtered. The filter cake was washed with dichloromethane/methanol (8:2; 2×100 mL) then the organic filtrates were combined and evaporated to dryness to give the title compound as a white solid (2.25 g, 87%). LC/MS: 3.41 min; z/e 361 and 363, calcd (M−1) 361 and 363. $^1$H NMR (400 MHz: CDCl$_3$): 7.40 (2H), 7.30 (5H), 7.15 (2H), 5.10 (2H), 4.05 (1H), 3.15 (1H), 2.70 (1H).

Intermediate 4

Benzyl 4-amino-3-(4-bromophenyl)-4-oxobutanoate

Di-iso-propylethylamine (3.21 g, 4.33 mL, 24.8 mmol) was added in one portion to a stirred suspension of 4-(benzyloxy)-2-(4-bromophenyl)-4-oxobutanoic acid (2.25 g, 6.21 mmol), ammonium chloride (0.332 g, 6.21 mmol) and N-[(Dimethylamino)-1H-1,2,3-triazolo[4,5-b]pyridin-1-ylmethylene]-N-methylmethanaminium hexafluorophosphate N-oxide (2.36 g, 6.21 mmol) in dimethylformamide (40 mL) at room temperature under nitrogen. After stirring for 2 h the volatiles were evaporated and the residue partitioned between dichloromethane (50 mL) and aqueous hydrochloric acid solution (1.0 M; 50 mL). The phases were separated and the aqueous layer washed with dichloromethane (2×50 mL). The organic phases were combined, dried (magnesium sulfate) and evaporated to dryness. The residue was chromatographed on silica gel (5% methanol: dichloromethane) to give the title compound as a white solid (1.14 g, 51%). LC/MS: 3.20 min; z/e 362 and 364, calcd (M+1) 362 and 364. $^1$H NMR (400 MHz: CDCl$_3$): 7.45 (2H), 7.30 (5H), 7.15 (2H), 5.45 (2H), 5.10 (2H), 3.95 (1H), 3.30 (1H), 2.70 (1H).

Intermediate 5

4-Amino-3-(4-bromophenyl)-4-oxobutanoic acid

A suspension of benzyl 4-amino-3-(4-bromophenyl)-4-oxobutanoate (1.14 g, 3.16 mmol) and platinum(IV) oxide (30 mg) in ethanol/ethyl acetate (5:1; 120 mL) was stirred under an hydrogen atmosphere for 2 h. After replacement of hydrogen with nitrogen the crude reaction mixture was filtered through a thin pad of celite and the filtrate evaporated to dryness to give the title compound as a white solid (671 mg, 78%). LC/MS: 2.41 min; z/e 271 and 273, calcd (M+1) 271 and 271. $^1$H NMR (400 MHz: DMSO-d$_6$): 7.50 (2H), 7.25 (2H), 3.95 (1H), 2.95 (1H), 2.45 (1H).

Intermediate 6

Benzyl (4-bromophenyl)acetate

4-Formylmorpholine (50 µL) was added to a stirred solution of 4-bromophenylacetic acid (5.00 g, 23.3 mmol) and oxalyl chloride (5.89 g, 4.05 mL, 46.6 mmol) in dichloromethane (30 mL) under nitrogen at room temperature. When gas evolution ceased the volatiles were evaporated and the residue was taken up in dichloromethane (30 mL). Benzyl alcohol (2.52 g, 2.41 mL, 23.3 mmol) was added in one portion and stirring was continued under nitrogen for 2 h. The volatiles were evaporated and the residue partitioned between dichloromethane (50 mL) and saturated sodium hydrogen carbonate solution (50 mL). The phases were separated and the aqueous phase was washed with dichloromethane (2×50 mL). The organic layers were combined, dried (magnesium sulfate) and the solvent evaporated. The residue was chromatographed on silica gel (20% diethyl ether: cyclohexane) to give the title compound as a white solid (6.76 g, 95%). LC/MS: 3.57 min; z/e 322 and 324, calcd (M+18) 322 and 324. $^1$H NMR (400 MHz: CDCl$_3$): 7.45 (2H), 7.30 (5H), 7.15 (2H), 5.15 (2H), 3.60 (2H).

Intermediate 7

1-Benzyl 4-tert-butyl 2-(4-bromophenyl)succinate

Lithium bis(trimethylsilyl)amide (1.06 M in THF; 20.6 mL, 21.9 mmol) was added dropwise over 10 min to a stirred solution of benzyl (4-bromophenyl)acetate (6.07 g, 19.9 mmol) in THF (60 mL) at −78° C. under nitrogen. On completion of addition stirring was continued at −78° C. for 30 min then t-butylbromoacetate (4.65 g, 3.52 mL, 23.9 mmol) was added dropwise over 5 min. The reaction was allowed to warm slowly to room temperature over 4 h then saturated ammonium chloride solution (50 mL) was added and the resulting suspension extracted with ethyl acetate (3×100 mL). The organic phases were combined, dried (magnesium sulfate) and evaporated to dryness. The residue was chromatographed on silica gel (10% diethyl ether: cyclohexane) to give the title compound as a colourless oil (6.82 g, 82%). LC/MS: 3.90 min; z/e 419 and 421, calcd (M+1) 419 and 421. $^1$H NMR (400 MHz: CDCl$_3$): 7.40 (2H), 7.30 (5H), 7.15 (2H), 5.10 (2H), 4.05 (1H), 3.05 (1H), 1.35 (9H).

Intermediate 8

4-(Benzyloxy)-3-(4-bromophenyl)-4-oxobutanoic acid

A suspension of 1-benzyl 4-tert-butyl 2-(4-bromophenyl)succinate (2.00 g, 4.77 mmol) and silica gel (23.8 g) in toluene (100 mL) was heated at reflux for 3 h. The crude mixture was cooled to room temperature and filtered. The filter cake was washed with dichloromethane/methanol (8:2; 2×100 mL) then the organic filtrates were combined and evaporated to dryness to give the title compound as a white solid (1.53 g, 88%). LC/MS: 3.43 min; z/e 361 and 363, calcd (M−1) 361 and 363. $^1$H NMR (400 MHz: DMSO-d$_6$): 7.55 (2H), 7.30 (7H), 5.10 (2H), 4.05 (1H), 3.05 (1H), 2.65 (1H).

Intermediate 9

Benzyl 4-amino-2-(4-bromophenyl)-4-oxobutanoate

Di-iso-propylethylamine (2.08 g, 2.80 mL, 16.0 mmol) was added in one portion to a stirred suspension of 4-(benzyloxy)-3-(4-bromophenyl)-4-oxobutanoic acid (1.45 g, 4.01 mmol), ammonium chloride (0.214 g, 4.01 mmol) and N-[(Dimethylamino)-1H-1,2,3-triazolo[4,5-b]pyridin-1-ylmethylene]-N-methylmethanaminium hexafluorophosphate N-oxide (1.68 g, 4.41 mmol) in dimethylformamide (20 mL) at room temperature under nitrogen. After stirring for 2 h the volatiles were evaporated and the residue partitioned between dichloromethane (50 mL) and aqueous hydrochloric acid solution (1.0 M; 50 mL). The phases were separated and the aqueous layer washed with dichloromethane (2×50 mL). The organic phases were combined, dried (magnesium sulfate) and evaporated to dryness. The residue was chromatographed on silica gel (10% methanol: dichloromethane) to give the title compound as a white solid (1.23 g, 85%). LC/MS: 3.14 min; z/e 362 and 364, calcd (M+1) 362 and 364. $^1$H NMR (400 MHz: DMSO-d$_6$): 7.55 (2H), 7.30 (8H), 6.85 (1H), 5.05 (2H), 4.05 (1H), 2.90 (1H), 2.50 (1H).

Intermediate 10

4-Amino-2-(4-bromophenyl)-4-oxobutanoic acid

A suspension of benzyl 4-amino-2-(4-bromophenyl)-4-oxobutanoate (1.53 g, 4.22 mmol) and platinum(IV) oxide (30 mg) in ethanol (100 mL) was stirred under an hydrogen atmosphere for 2 h. After replacement of hydrogen with nitrogen the crude reaction mixture was filtered through a thin pad of celite and the filtrate evaporated to dryness to give the title compound as a cream coloured solid (1.14 g, 100%). LC/MS: 2.36 min; z/e 272 and 274, calcd (M+1) 272 and 274. $^1$H NMR (400 MHz: DMSO-d$_6$): 7.50 (2H), 7.30 (1H), 7.20 (2H), 6.80 (1H), 3.90 (1H), 2.80 (1H), 2.40 (1H).

Intermediate 11

[4-(Isopentyloxy)phenyl]acetic acid

Aqueous sodium hydroxide solution (2.0 M; 32.9 mL, 65.8 mmol) was added in one portion to a stirred solution of p-hydroxyphenylacetic acid (5.00 g, 32.9 mmol) in ethanol (200 mL) at room temperature. After stirring for 15 min 1-bromo-3-methylbutane (4.97 g, 3.94 mL, 32.9 mmol) was added in one portion and the resulting solution heated at reflux for 12 h. The reaction was cooled to room temperature then evaporated to dryness. The residue was partitioned between dichloromethane (150 mL) and aqueous hydrochloric acid solution (1.0 M; 150 mL). The layers were separated and the aqueous phase was washed with dichloromethane (2×100 mL). The organic extracts were combined, dried (magnesium sulfate) and evaporated to dryness. The resulting white solid residue was used without purification in the preparation of R8782/83/1. LC/MS: 3.30 min; z/e 221, calcd (M−1) 221. $^1$H NMR (400 MHz: CDCl$_3$): 7.25 (2H), 6.95 (2H), 4.05 (2H), 3.65 (2H), 1.95 (1H), 1.75 (2H), 1.05 (6H). The absolute regiochemistry of the product was unambiguously assigned using an HMBC correlation experiment.

Intermediate 12 tert-Butyl [4-(isopentyloxy)phenyl]acetate

Boron trifluoride etherate (0.65 mL) was added in one portion to a stirred solution of [4-(isopentyloxy)phenyl]acetic acid (crude from preparation of intermediate 11; 7.31 g, 32.9 mmol) and t-butyltrichloroacetimidate (14.4 g, 11.8 mL, 65.8 mmol) in THF (70 mL) at room temperature under nitrogen. The resulting solution was stirred for 16 h then quenched with saturated aqueous sodium hydrogen carbonate solution (50 mL). The resulting suspension was extracted with ethyl acetate (3×50 mL) then the organic extracts combined, dried (magnesium sulfate) and evaporated to dryness. The residue was chromatographed on silica gel (5-10% diethyl ether: cyclohexane) to give the title compound as a colourless oil (3.82 g, 42% over 2 steps). LC/MS: 3.94 min; z/e 296, calcd (M+18) 296. $^1$H NMR (400 MHz: CDCl$_3$): 7.25 (2H), 6.90 (2H), 4.05 (2H), 3.55 (2H), 1.90 (1H), 1.75 (2H), 1.50 (9H), 1.05 (6H).

Intermediate 13

4-Benzyl 1-tert-butyl 2-[4-(isopentyloxy)phenyl]succinate

Lithium bis(trimethylsilyl)amide (1.06 M in THF; 7.11 mL, 7.54 mmol) was added dropwise over 10 min to a stirred solution of tert-butyl [4-(isopentyloxy)phenyl]acetate (2.00 g, 7.18 mmol) in THF (25 mL) at −78° C. under nitrogen. On completion of addition stirring was continued at −78° C. for 30 min then benzyl-2-bromoacetate (1.97 g, 1.36 mL, 8.61 mmol) was added dropwise over 5 min. The reaction was allowed to warm slowly to room temperature over 4 h. Once at room temperature saturated ammonium chloride solution (25 mL) was added and the resulting suspension extracted with ethyl acetate (3×50 mL). The organic phases were combined, dried (magnesium sulfate) and evaporated to dryness. The residue was chromatographed on silica gel (5-10% diethyl ether: cyclohexane) to give the title compound as a colourless oil (2.00 g, 66%). LC/MS: 4.20 min; z/e 427, calcd (M+1) 427. $^1$H NMR (400 MHz: CDCl$_3$): 7.35 (5H), 7.2 (2H), 6.80 (2H), 5.10 (2H), 3.95 (3H), 3.15 (1H), 2.65 (1H), 1.85 (1H), 1.65 (2H), 1.45 (9H), 0.95 (6H).

Intermediate 14

4-(Benzyloxy)-2-[4-(isopentyloxy)phenyl]-4-oxobutanoic acid

A suspension of 4-benzyl 1-tert-butyl 2-[4-(isopentyloxy)phenyl]succinate (2.00 g, 4.69 mmol) and silica gel (23.4 g) in toluene (150 mL) was heated at reflux for 3 h. The crude mixture was cooled to room temperature and filtered. The filter cake was washed with dichloromethane/methanol (8:2; 2×100 mL) then the organic filtrates were combined and evaporated to dryness to give the title compound as white solid (1.41 g, 82%). LC/MS: 3.74 min; z/e 388, calcd (M+1) 388. The enantiomers were separated using a Chiralpak AD column (20% EtOH: Heptane: 0.1% TFA), Flow 20 mL/min, λ=215 nM Ent-1=12.5 min, Ent-2=15.0 min.

Intermediate 15

Methyl [4-(isopentyloxy)phenyl]acetate

Methyl-4-hydroxyphenylacetate (2.00 g, 12.0 mmol) was added in one portion to a stirred suspension of sodium hydride (60% mineral oil suspension; 528 mg, 13.2 mmol) in dimethylformamide (20 mL) at room temperature under nitrogen. After stirring for 30 min 1-bromo-3-methylbutane (1.99 g, 1.58 mL, 13.2 mmol) was added dropwise over 5 min then stirring was continued for 12 h. The volatiles were evaporated then the residue partitioned between dichloromethane (50 mL) and water (50 mL). The phases were separated and the aqueous phase was washed with dichloromethane (2×50 mL). The organics were combined, dried (magnesium sulfate) and the solvent evaporated. The residue was chromatographed on silica gel (20% diethyl ether: cyclohexane) to give the title compound as a colourless oil (2.16 g, 76%). LC/MS: 3.51 min; z/e 254, calcd (M+18) 254. $^1$H NMR (400 MHz: CDCl$_3$): 7.15 (2H), 6.85 (2H), 4.00 (2H), 3.70 (3H), 3.55 (2H), 1.85 (1H), 1.70 (2H), 0.95 (6H).

Intermediate 16

4-tert-Butyl 1-methyl 2-[4-(isopentyloxy)phenyl]succinate

Lithium bis(trimethylsilyl)amide (1.06 M in THF; 9.43 mL, 10.0 mmol) was added dropwise over 10 min to a stirred solution of methyl [4-(isopentyloxy)phenyl]acetate (2.15 g, 9.10 mmol) in THF (30 mL) at −78° C. under nitrogen. On completion of addition stirring was continued at −78° C. for 30 min then t-butylbromoacteate (2.12 g, 1.61 mL, 10.9 mmol) was added dropwise over 5 min. The reaction was allowed to warm slowly to room temperature over 4 h then saturated ammonium chloride solution (30 mL) was added and the resulting suspension extracted with ethyl acetate (3×50 mL). The organic phases were combined, dried (magnesium sulfate) and evaporated to dryness. The residue was chromatographed on silica gel (20% diethyl ether: cyclohexane) to give the title compound as a colourless oil (2.69 g, 85%). LC/MS: 3.80 min; z/e 351, calcd (M+1) 351. $^1$H NMR (400 MHz: CDCl$_3$): 7.20 (2H), 6.85 (2H), 3.95 (3H), 3.65 (3H), 3.05 (1H), 2.55 (1H), 1.85 (1H), 1.70 (2H), 1.40 (9H), 0.95 (6H).

Intermediate 17

Benzyl (4-hydroxyphenyl)acetate

Prepared using the procedure of O. Brümmer, T. Z. Hoffman, D-W. Chen, K. D. Janda, *Chem. Commun.* 2001, 19-20.

Intermediate 18

Benzyl (4-{[tert-butyl(dimethyl)silyl]oxy}phenyl)acetate t-Butyldimethylsilyl chloride (3.07 g, 20.4 mmol) was added in one portion to a stirred solution of benzyl (4-hydroxyphenyl)acetate (4.70 g, 19.4 mmol) and imidazole (1.39 g, 20.4 mmol) in dimethylformamide (25 mL) at room temperature under nitrogen. After stirring for 4 h the volatiles were evaporated and the residue partitioned between water (100 mL) and ethyl acetate (100 mL). The layers were separated and the aqueous phase washed with ethyl acetate (2×100 mL). The organic extracts were combined, dried (magnesium sulfate) and the solvent evaporated. The residue was chromatographed on silica gel (10% diethyl ether: cyclohexane) to give the title compound as a colourless oil (4.32 g, 62%). LC/MS: 4.13 min; z/e 374, calcd (M+18) 374. $^1$H NMR (400 MHz: CDCl$_3$): 7.15 (5H), 6.95 (2H), 6.60 (2H), 4.95 (2H) 3.40 (2H), 0.8 (9H), 0.00 (6H).

Intermediate 19

1-Benzyl 4-tert-butyl 2-(4-{[tert-butyl(dimethyl)silyl]oxy}phenyl)succinate

Lithium bis(trimethylsilyl)amide (1.06 M in THF; 12.6 mL, 13.3 mmol) was added dropwise over 10 min to a stirred solution of benzyl (4-{[tert-butyl(dimethyl)silyl]oxy}phenyl)acetate (4.32 g, 12.1 mmol) in THF (40 mL) at −78° C. under nitrogen. On completion of addition stirring was continued at −78° C. for 30 min then t-butylbromoacetate (2.82 g, 2.14 mL, 14.5 mmol) was added dropwise over 5 min. The reaction was allowed to warm slowly to room temperature over 4 h then saturated ammonium chloride solution (40 mL) was added and the resulting suspension extracted with ethyl acetate (3×50 mL). The organic phases were combined, dried (magnesium sulfate) and evaporated to dryness. The residue was chromatographed on silica gel (5% diethyl ether: cyclohexane) to give the title compound as a colourless oil (5.35 g, 94%). LC/MS: 4.35 min; z/e 488, calcd (M+18) 488. $^1$H NMR (400 MHz: CDCl$_3$): 7.10 (3H), 7.05 (2H), 6.95 (2H), 6.60 (2H), 4.95 (2H), 3.85 (1H), 2.90 (1H), 2.40 (1H) 1.20 (9H), 0.8 (9H), 0.05 (6H).

Intermediate 20

4-(Benzyloxy)-3-(4-{[tert-butyl(dimethyl)silyl]oxy}phenyl)-4-oxobutanoic acid A suspension of 1-benzyl 4-tert-butyl 2-(4-{[tert-butyl(dimethyl)silyl]oxy}phenyl)succinate (1.00 g, 2.12 mmol) and silica gel (10.6 g) in toluene (50 mL) was heated at reflux for 3 h. The crude mixture was cooled to room temperature and filtered. The filter cake was washed with dichloromethane/methanol (8:2; 2×100 mL) then the organic filtrates were combined and evaporated to dryness to give the title compound as a while solid (0.83 g, 94%). LC/MS: 4.03 min; z/e 432, calcd (M+18) 432. $^1$H NMR (400 MHz: DMSO-d$_6$): 7.05 (7H), 6.60 (2H), 4.95 (2H), 3.85 (1H), 2.85 (1H), 2.40 (1H), 0.80 (9H), 0.00 (6H).

Intermediate 21

Benzyl 4-amino-2-(4-hydroxyphenyl)-4-oxobutanoate

Di-iso-propylethylamine (1.03 g, 1.40 mL, 8.00 mmol) was added in one portion to a stirred suspension of 4-(benzyloxy)-3-(4-{[tert-butyl(dimethyl)silyl]oxy}phenyl)-4-oxobutanoic acid (0.83 g, 2.0 mmol), ammonium chloride (0.107 g, 2.00 mmol) and N-[(Dimethylamino)-1H-1,2,3-triazolo[4,5-b]pyridin-1-ylmethylene]-N-methylmethanaminium hexafluorophosphate N-oxide (837 mg, 2.20 mmol) in dimethylformamide (15 mL) at room temperature under nitrogen. After stirring for 2 h the volatiles were evaporated and the residue partitioned between dichloromethane (50 mL) and aqueous hydrochloric acid solution (1.0 M; 50 mL). The resulting bi-phasic mixture was stirred at room temperature for 30 min after which the phases were separated and the aqueous layer washed with dichloromethane (2×50 mL). The organic layers were combined, dried (magnesium sulfate) and evaporated to dryness. The residue was chromatographed on silica gel (10% methanol: dichloromethane) to give the title compound as a white solid (0.45 g, 60%). LC/MS: 2.55 min; z/e 300, calcd (M+1) 300. $^1$H NMR (400 MHz: CDCl$_3$): 7.25 (3H), 7.15 (2H), 7.10 (2H), 6.75 (2H), 6.35 (1H), 6.65 (1H), 5.45 (1H), 5.10 (2H), 4.10 (1H), 3.05 (1H), 2.55 (1H).

Intermediate 22

4-Amino-2-(4-hydroxyphenyl)-4-oxobutanoic acid

A suspension of benzyl 4-amino-2-(4-hydroxyphenyl)-4-oxobutanoate (327 mg, 1.09 mmol) and palladium on charcol (10%, 50 mg) in ethanol (30 mL) was stirred under a hydrogen atmosphere for 2 h. After replacement of hydrogen with nitrogen the crude reaction mixture was filtered through a thin pad of celite and the filtrate evaporated to dryness to give the title compound as a white solid (229 mg, 100%). LC/MS: 0.81 min; z/e 210, calcd (M+1) 210. $^1$H NMR (400 MHz: DMSO-d$_6$): 11.9 (1H), 9.10 (1H), 7.10 (1H), 6.85 (2H), 6.55 (1H), 6.50 (2H), 3.60 (1H), 2.60 (1H), 2.15 (1H).

EXAMPLE 1

4-Amino-3-(4'-cyano-1,1'-biphenyl-4-yl)-4-oxobutanoic acid

A solution of 4-amino-3-(4-bromophenyl)-4-oxobutanoic acid (10 mg, 37 µmol) in dimethoxyethane (1 mL) was added in one portion to a mixture of p-nitrilebenzeneboronic acid (5.4 mg, 36 µmol) and fibrecat FC1001 (2.71% Pd; 14 mg, 3.7 µmol) in a Smith microwave reaction vial. Aqueous sodium carbonate solution (1.0 M; 73 µL, 73 µmol) was added and the vial capped. The crude reaction mixture was heated at 150° C. for 15 min using a Smith Synthesiser microwave reactor. On cooling the vial was opened and the contents filtered through a Whatman 5 µM filter tube, washing the filter cake with methanol (2×1 mL). The filtrate was evaporated and the resulting residue was purified using mass directed auto-preparative reverse phase HPLC to give the title compound (1.1 mg, 10%) as a white solid. LC/MS: 2.67 min; z/e 295, calcd (M+1) 295. $^1$H NMR (400 MHz: DMSO-d$_6$): 7.80 (4H), 7.60 (2H), 7.50 (2H), 4.05 (1H), 3.10 (1H), 2.65 (1H).

EXAMPLE 2

4-Amino-4-oxo-3-[4'-(trifluoromethyl)-1,1'-biphenyl-4-yl]butanoic acid

Prepared by an analogous reaction sequence to example 1—except using dimethoxyethane/water (1:1; 1 mL) as reaction solvent. LC/MS: 3.12 min; z/e 338, calcd (M+1) 338.

EXAMPLE 3

3-(3'-Acetyl-1,1'-biphenyl-4-yl)-4-amino-4-oxobutanoic acid

Prepared by an analogous reaction sequence to example 1—except using dimethoxyethane/water (1:1; 1 mL) as reaction solvent. LC/MS: 2.59 min; z/e 312, calcd (M+1) 312.

EXAMPLE 4

4-Amino-3-(1,1'-biphenyl-4-yl)-4-oxobutanoic acid

Prepared by an analogous reaction sequence to example 1—except using dimethoxyethane/water (1:1; 1 mL) as reaction solvent. LC/MS: 2.77 min; z/e 270, calcd (M+1) 270.

EXAMPLE 5

4-Amino-3-(3'-cyano-1,1'-biphenyl-4-yl)-4-oxobutanoic acid

Prepared by an analogous reaction sequence to example 1. LC/MS: 2.67 min; z/e 295, calcd (M+1) 295.

EXAMPLE 6

4-Amino-4-oxo-3-(4-thien-3-ylphenyl)butanoic acid

Prepared by an analogous reaction sequence to example 1—except using dimethoxyethane/water (1:1; 1 mL) as reaction solvent. LC/MS: 2.68 min; z/e 276, calcd (M+1) 276.

EXAMPLE 7

4-Amino-3-[4-(1H-indol-5-yl)phenyl]-4-oxobutanoic acid

Prepared by an analogous reaction sequence to example 1—except using dimethoxyethane/water (1:1; 1 mL) as reaction solvent. LC/MS: 2.71 min; z/e 309, calcd (M+1) 309.

EXAMPLE 8

4-Amino-2-(4'-cyano-1,1'-biphenyl-4-yl)-4-oxobutanoic acid

A solution of 4-amino-2-(4-bromophenyl)-4-oxobutanoic acid (10 mg, 37 µmol) in dimethoxyethane (1 mL) was added in one portion to a mixture of 4-nitrilebenzeneboronic acid (5.4 mg, 36 µmol) and fibrecat FC1001 (2.71 % Pd; 14 mg, 3.7 µmol) in a Smith microwave reaction vial. Aqueous sodium carbonate solution (1.0M; 73 µL, 73 µmol) was added and the vial capped. The crude reaction mixture was heated at 150° C. for 15 min using a Smith Synthesiser microwave reactor. On cooling the vial was opened and the contents filtered through a Whatman 5 µM filter tube washing the filter cake with methanol (2×1 mL). The filtrate was evaporated and the resulting residue was purified using mass directed auto-preparative reverse phase HPLC to give the title compound (1.6 mg, 15%) as a white solid. LC/MS: 2.70 min; z/e 295, calcd (M+1) 295. $^1$H NMR (400 MHz: DMSO-$d_6$): 7.80 (4H), 7.60 (2H), 7.50 (2H), 4.10 (1H), 3.05 (1H), 2.65 (1H).

EXAMPLE 9

4-Amino-4-oxo-2-[4'-(trifluoromethoxy)-1,1'-biphenyl-4-yl]butanoic acid

Prepared by an analogous reaction sequence to example 8. LC/MS: 3.16 min; z/e 354, calcd (M+1) 354.

EXAMPLE 10

2-(4'-Acetyl-1,1'-biphenyl-4-yl)-4-amino-4-oxobutanoic acid

Prepared by an analogous reaction sequence to example 8. LC/MS: 2.58 min; z/e 312, calcd (M+1) 312.

EXAMPLE 11

2-(3'-Acetyl-1,1'-biphenyl-4-yl)-4-amino-4-oxobutanoic acid

Prepared by an analogous reaction sequence to example 8. LC/MS: 2.57 min; z/e 312, calcd (M+1) 312.

EXAMPLE 12

4-Amino-2-(4'-methoxy-1,1'-biphenyl-4-yl)-4-oxobutanoic acid

Prepared by an analogous reaction sequence to example 8. LC/MS: 2.76 min; z/e 300, calcd (M+1) 300.
3.20 (1H), 2.70 (1H), 1.85 (1H), 1.70 (2H), 0.95 (6H). The enantiomers were separated using a Chiralpak AD column (5% EtOH:Heptane:0.1% TFA), Flow 15 mL/min, λ=215 nM Ent-1=14 min, Ent-2=18 min.

EXAMPLE 13

4-Amino-2-[4-(2-cyclohexylethoxy)phenyl]-4-oxobutanoic acid

Aqueous sodium hydroxide solution (2.0 M; 50 µL, 100 µmol) was added in one portion to a stirred solution of 4-amino-2-(4-hydroxyphenyl)-4-oxobutanoic acid (10 mg, 47 µmol) in ethanol (1 mL) at room temperature. After stirring for 10 min cyclohexylethylbromide (9.0 mg, 47 µmol) was added and the resulting mixture heated at reflux for 12 h. On cooling to room temperature the volatiles were evaporated and the residue purified by mass directed auto-preparative reverse phase HPLC to give the title compound as a white solid (2.1 mg, 14%). LC/MS: 3.34 min; z/e 320, calcd (M+1) 320. $^1$H NMR (400 MHz: MeOD): 7.20 (2H), 6.85 (2H), 4.00 (3H), 2.95 (1H), 2.55 (1H), 1.70 (6H), 1.50 (1H), 1.25 (4H), 0.92 (2H). The absolute regiochemistry of the product was unambiguously assigned using an HMBC correlation experiment.

What is claimed is:

1. A compound of formula (I):

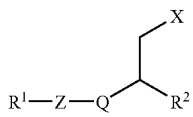
(I)

wherein:

$R^1$ is optionally substituted —$C_{4-12}$ alkyl, —$C_{2-10}$alkylcycloalkyl, —$C_{2-6}$alkylheterocycloalkyl, —$C_{2-6}$alkylaryl, optionally substituted 5- or 6-membered aryl or heteroaryl, provided that $R^1$ is not pyridinyl;

Z is a bond, $CH_2$, O, S, SO, $SO_2$, $NR^4$, $OCR^4R^5$ or $CR^4R^5O$; or Z, $R^1$ and Q together form an optionally substituted fused tricyclic group;

Q is unsubstituted phenyl;

X is COOH;

$R^2$ is $CONH_2$;

$R^4$ and $R^5$ each independently is H, $C_{1-6}$ alkyl or $C_{1-4}$ alkylaryl; or ester, amides and carbamates, salt and solvates thereof; and further provided that when $R^1$ is $C_{4-12}$alkyl, Z is other than a bond, O or $CH_2$.

2. A compound according to claim 1, wherein Z represents a bond or O.

3. A compound according to claim 1, of formula (Ia):

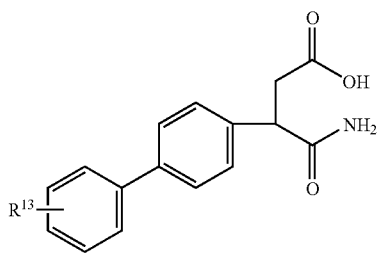
(Ia)

wherein:

$R^{13}$ is H, halo, $CF_3$, —$OCF_3$, cyano, nitro, $OR^{14}$, $SR^{15}$ or $COR^{16}$; and $R^{14}$, $R^{15}$, $R^{16}$ independently are H, $C_{1-6}$ alkyl or $C_{1-4}$ alkylaryl; or ester, amides and carbamates, salts and solvates thereof.

4. A composition comprising a compound according to claim 1 and a pharmaceutically acceptable carrier.

5. A process for preparation of compounds of formula (I) as defined in claim 1, wherein the process comprises:

(A) preparing a compound of formula (I), wherein Z is a bond and $R^1$ is an optionally substituted 5- or 6-membered aryl or heteroaryl, by reacting a compound of formula (II):

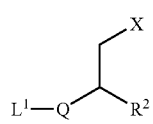
(II)

wherein $R^2$, Q and X are as previously defined for formula (I) and $L^1$ is a leaving group, with a reagent suitable to introduce the group $R^1$; or (B)(i) preparing a compound of formula (I), wherein Z is O, S, SO, $SO_2$, $NR^4$ or $OCR^4R^5$, by reacting a compound of formula (III):

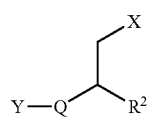
(III)

wherein $R^2$, Q and X are as previously defined for formula (I) and Y is OH, SH, $NHR^4$ or $HOCR^4R^5$, with a compound of formula (IV):

(IV)

wherein $R^1$ is defined above for compounds of formula (I) and $L^2$ represents a leaving group; and (ii) wherein Y is —SH, optionally followed by oxidizing the Y group to the corresponding SO or $SO_2$ group as required; or (C) preparing a compound of formula (I), wherein Z is —$CR^4R^5O$—, by reacting a compound of formula (III), wherein Y is —OH, with a compound of formula (V):

(V)

wherein $R^1$ $R^4$, $R^5$ are defined above for compounds of formula (I) and $L^3$ represents a leaving group; or (D) preparing a compound of formula (I), wherein Z is $CH_2$ and $R^1$ is an optionally substituted 5- or 6-membered aryl or heteroaryl, by reacting
(i) a compound of formula (VI):

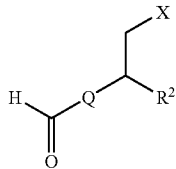
(VI)

wherein Q, X and $R^2$ are as defined above, with an optionally substituted 5- or 6-membered aryl or heteroaryl nucleophile, which is a compound of formula (VII):

$$R^{17}\text{-A-M} \qquad (VII)$$

wherein A is a 5- or 6-membered aryl or heteroaryl, $R^{17}$ is H or one or more substituents and M is a metal and
(ii) reducing and eliminating a resultant or product alcohol formed form step (i); and, (E) optionally deprotecting compounds of formula (I) with a protecting group.

* * * * *

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Fluorescent peptide substrate

<400> SEQUENCE: 1

Gly Pro Leu Gly Leu Phe Ala Arg Lys
1               5
```